(12) United States Patent
Howe et al.

(10) Patent No.: US 10,525,305 B2
(45) Date of Patent: Jan. 7, 2020

(54) METHOD AND SYSTEM FOR INTERPRETING ACTIVITY OF A PERSON ON A FLEXIBLE MAT OF A TRAMPOLINE

(71) Applicant: TGOMA NZ LIMITED, Christchurch (NZ)

(72) Inventors: John Robert Howe, Christchurch (NZ); Neil Adrian Trimboy, Rangiora (NZ)

(73) Assignee: TGOMA NZ LIMITED, Christchurch (NZ)

( * ) Notice: Subject to any disclaimer, the term of this patent is extended or adjusted under 35 U.S.C. 154(b) by 78 days.

(21) Appl. No.: 15/322,773

(22) PCT Filed: Jul. 3, 2015

(86) PCT No.: PCT/IB2015/055015
§ 371 (c)(1),
(2) Date: Dec. 29, 2016

(87) PCT Pub. No.: WO2016/001880
PCT Pub. Date: Jan. 7, 2016

(65) Prior Publication Data
US 2017/0128779 A1   May 11, 2017

Related U.S. Application Data

(60) Provisional application No. 62/019,449, filed on Jul. 1, 2014.

(51) Int. Cl.
*A63B 24/00* (2006.01)
*A63B 71/06* (2006.01)
(Continued)

(52) U.S. Cl.
CPC ............ *A63B 24/0021* (2013.01); *A63B 5/11* (2013.01); *A63B 24/0075* (2013.01);
(Continued)

(58) Field of Classification Search
CPC ....... A63B 5/11; A63B 24/00; A63B 24/0021; A63B 24/0059; A63B 24/0084;
(Continued)

(56) References Cited

U.S. PATENT DOCUMENTS 5,469,740 A * 11/1995 French ................ A61B 5/1036
273/445
2005/0043122 A1* 2/2005 Publicover ............... A63B 5/11
473/465

(Continued)

FOREIGN PATENT DOCUMENTS

CA    2772801    9/2012
EP    1576987    9/2005
(Continued)

OTHER PUBLICATIONS

21st Century Innovative Students Creative Thinking Training New Concept (vol. 2), Aug. 31, 2000, pp. 1-4.

*Primary Examiner* — Loan B Jimenez
*Assistant Examiner* — Shila Jalalzadeh Abyaneh
(74) *Attorney, Agent, or Firm* — Dann, Dorfman, Herrell and Skillman, P.C.

(57) ABSTRACT

A method of interpreting an activity of a person on a flexible mat of a trampoline, the method comprising: at least one processor determining a bounce instruction for the person on the flexible mat; determining a first bounce location of the person on the flexible mat; determining a second bounce location of the person on the flexible mat; determining a lead time boundary interval; responsive to determining a time of display of the bounce instruction prior to the lead time boundary interval, the at least one processor comparing the second bounce location with the bounce instruction; and responsive to determining a time of display of the bounce instruction within the lead time boundary interval, the at least one processor determining a third bounce location of (Continued)

the person on the flexible mat and comparing the third bounce location with the bounce instruction.

35 Claims, 11 Drawing Sheets

(51) Int. Cl.
| | |
|---|---|
| *A63B 5/11* | (2006.01) |
| *A63F 13/816* | (2014.01) |
| *A63B 71/02* | (2006.01) |
| *A63F 13/25* | (2014.01) |
| *A61B 5/103* | (2006.01) |
| *A63F 13/24* | (2014.01) |
| *A61B 5/00* | (2006.01) |
| *A61B 5/11* | (2006.01) |
| *A63F 13/655* | (2014.01) |
| *A63F 13/213* | (2014.01) |
| *A63B 21/02* | (2006.01) |

(52) U.S. Cl.
CPC ........ *A63B 71/022* (2013.01); *A63B 71/0622* (2013.01); *A63F 13/24* (2014.09); *A63F 13/25* (2014.09); *A63B 2024/0037* (2013.01); *A63B 2220/12* (2013.01); *A63B 2220/13* (2013.01); *A63B 2220/40* (2013.01); *A63B 2225/50* (2013.01)

(58) Field of Classification Search
CPC ............ A63B 24/0075; A63B 71/0669; A63B 71/022; A63B 71/0622; A63B 2024/0037; A63B 21/026; A63B 2210/50; A63B 2225/50; A63B 2220/40; A63B 2220/30; A63B 2220/13; A63B 2220/05; A63B 2071/0658; A63B 2220/20; A63B 2220/12; A63F 13/24; A63F 13/25; A63F 13/816; A63F 13/213; A63F 13/655; A61B 5/11; A61B 5/744; A61B 5/742; A61B 5/6895; A61B 5/6892; A61B 2562/046; A61B 2562/0261; A61B 2562/0247; A61B 2562/0219; A61B 5/1128; A61B 5/1113; A61B 5/1036; A61B 5/0059

See application file for complete search history.

(56) References Cited

U.S. PATENT DOCUMENTS

| | | | | |
|---|---|---|---|---|
| 2005/0209053 | A1* | 9/2005 | Knox | ............... A63B 5/11 482/27 |
| 2011/0034300 | A1* | 2/2011 | Hall | ............... A63B 5/11 482/1 |
| 2015/0335930 | A1* | 11/2015 | Dallmann | ......... A63B 71/0622 482/27 |

FOREIGN PATENT DOCUMENTS

| | | |
|---|---|---|
| WO | 9932889 | 7/1999 |
| WO | 2011121356 | 10/2011 |
| WO | 2014098628 | 6/2014 |

\* cited by examiner

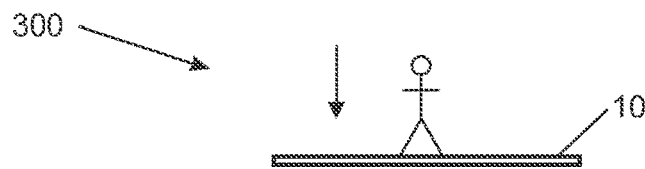
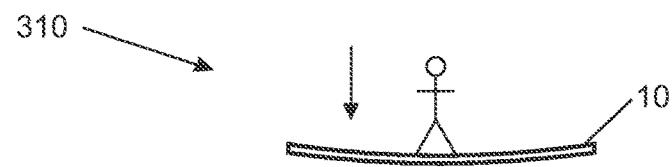
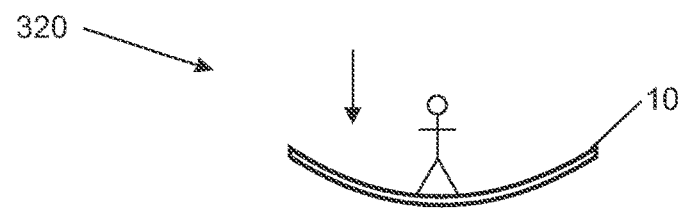
FIGURE 3
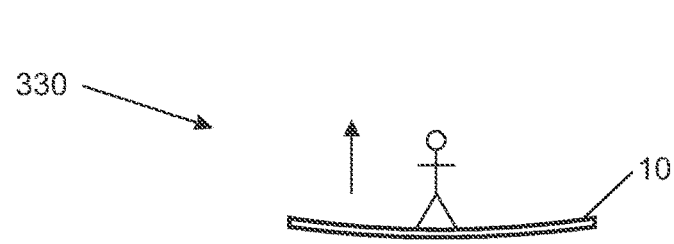
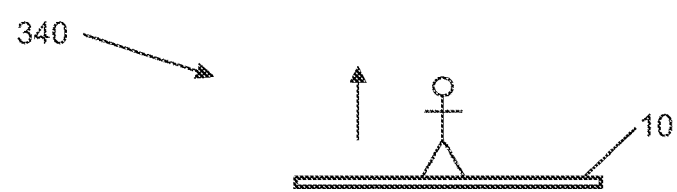

METHOD AND SYSTEM FOR INTERPRETING ACTIVITY OF A PERSON ON A FLEXIBLE MAT OF A TRAMPOLINE

FIELD OF INVENTION

The invention relates to techniques and apparatus for interpreting activity on a flexible mat of a trampoline. The invention particularly relates to techniques and apparatus for interpreting a bounce of a person on the flexible mat.

In another aspect the invention relates to game or other interactive apparatus for providing information and/or entertainment to a person based on activity of the person on a flexible mat of the trampoline.

BACKGROUND

Canadian patent publication CA 2,772,801 to Yjip Inc describes a trampoline including a frame and a jumping mat assembly that is supported by the frame to allow at least one user to bounce on the jumping mat. The trampoline also includes a sensor system that includes a plurality of sensors supported by the frame and/or the jumping mat assembly. The sensors are used to determine the status of a user or users on the trampoline.

The plurality of sensors are typically spaced apart from each other. A single bouncing load of the user triggers multiple sensors simultaneously. The multiple sensors can output different signals depending on the spatial relationship between the bouncing load and the particular sensor. The signals from the multiple sensors are compared to provide a location of the user on the trampoline.

A potential drawback with the prior art is the inability to determine the appropriate time to issue a bounce instruction to a user to both enable and challenge the user to carry out the bounce instruction. If the timing of bounce instructions is wrong, this has the potential to lead to a high error rate in user compliance with bounce instructions. This in turn has the potential for reduced interaction performance and a poor user experience.

Furthermore, there is no ability to calculate the duration of time a user spends in the air or on the jumping mat.

It is an object of preferred embodiments of the present invention to address some of the aforementioned disadvantages. An additional or alternative object is to at least provide the public with a useful choice.

SUMMARY OF THE INVENTION

In broad terms in one aspect the invention comprises a method of interpreting an activity of a person on a flexible mat of a trampoline, the method comprising at least one processor determining a bounce instruction for the person on the flexible mat; determining a first bounce location of the person on the flexible mat; determining a second bounce location of the person on the flexible mat; determining a lead time boundary interval; responsive to determining a time of display of the bounce instruction prior to the lead time boundary interval, the at least one processor comparing the second bounce location with the bounce instruction; and responsive to determining a time of display of the bounce instruction within the lead time boundary interval, the at least one processor determining a third bounce location of the person on the flexible mat and comparing the third bounce location with the bounce instruction.

The term 'comprising' as used in this specification and claims means 'consisting at least in part of'. When interpreting statements in this specification and claims which include the term 'comprising', other features besides the features prefaced by this term in each statement can also be present. Related terms such as 'comprise' and 'comprised' are to be interpreted in similar manner.

Preferably the method further comprises a display in communication with the at least one processor displaying a representation of the bounce instruction.

Preferably the bounce instruction comprises a bounce location instruction.

Preferably the representation of the bounce instruction comprises two or more bounce location targets, at least one of the bounce location targets presented so as to draw the attention of the user in order to present a bounce instruction to the user.

Preferably the representation of the bounce instruction comprises a virtual environment and at least one bounce location target within the virtual environment.

Preferably the bounce instruction comprises a bounce time interval instruction.

Preferably the bounce instruction comprises a bounce location instruction and a bounce time interval instruction.

Preferably the bounce time interval instruction comprises an instruction for the user to contact the flexible mat during a time interval.

Preferably the bounce time interval instruction comprises an instruction for the user to avoid contact with the flexible mat during a time interval.

Preferably the first bounce location, the second bounce location, and/or the third bounce location is/are determined by at least one sensor in physical connection with the flexible mat.

Preferably the first bounce location, the second bounce location, and/or the third bounce location is/are determined by at least one visual sensor directed toward the flexible mat.

Preferably the first bounce location, the second bounce location, and/or the third bounce location is/are determined by at least one device in physical connection with the user.

In another aspect the invention comprises a method of instructing an activity of a person on a flexible mat of a trampoline, the method comprising receiving a first bounce location of the person on the flexible mat; displaying a representation of a bounce instruction to the person on the flexible mat; receiving a second bounce location of the person on the flexible mat; responsive to determining a time of display of the bounce instruction prior to a lead time boundary interval, at least one processor comparing the second bounce location with the bounce instruction; and responsive to determining a time of display of the bounce instruction within the lead time boundary interval, the at least one processor comparing a third bounce location with the bounce instruction.

Preferably the bounce instruction comprises a bounce location instruction.

Preferably the representation of the bounce instruction comprises two or more bounce location targets, at least one of the bounce location targets presented so as to draw the attention of the user in order to present a bounce instruction to the user.

Preferably the representation of the bounce instruction comprises a virtual environment and at least one bounce location target within the virtual environment.

Preferably the bounce instruction comprises a bounce time interval instruction.

Preferably the bounce instruction comprises a bounce location instruction and a bounce time interval instruction.

Preferably the bounce time interval instruction comprises an instruction for the user to contact the flexible mat during a time interval.

Preferably the bounce time interval instruction comprises an instruction for the user to avoid contact with the flexible mat during a time interval.

Preferably the first bounce location, the second bounce location, and/or the third bounce location is/are determined by at least one sensor in physical connection with the flexible mat.

Preferably the first bounce location, the second bounce location, and/or the third bounce location is/are determined by at least one visual sensor directed toward the flexible mat.

Preferably the first bounce location, the second bounce location, and/or the third bounce location is/are determined by at least one device in physical connection with the user.

In another aspect the invention comprises a system comprising at least one processor configured to: receive a first bounce location of a person on a flexible mat of a trampoline; receive a second bounce location of the person on the flexible mat; responsive to determining a time of display of a bounce instruction prior to a lead time boundary interval, comparing the second bounce location with the bounce instruction; and responsive to determining a time of display of the bounce instruction within the lead time boundary interval, receiving a third bounce location of the person on the flexible mat and comparing the third bounce location with the bounce instruction.

Preferably the system further comprises a display in communication with the at least one processor, the display configured to display a representation of the bounce instruction.

Preferably the bounce instruction comprises a bounce location instruction.

Preferably the representation of the bounce instruction comprises two or more bounce location targets, at least one of the bounce location targets presented so as to draw the attention of the user in order to present a bounce instruction to the user.

Preferably the representation of the bounce instruction comprises a virtual environment and at least one bounce location target within the virtual environment.

Preferably the bounce instruction comprises a bounce time interval instruction.

Preferably the bounce instruction comprises a bounce location instruction and a bounce time interval instruction.

Preferably the bounce time interval instruction comprises an instruction for the user to contact the flexible mat during a time interval.

Preferably the bounce time interval instruction comprises an instruction for the user to avoid contact with the flexible mat during a time interval.

Preferably the first bounce location, the second bounce location, and/or the third bounce location is/are determined by at least one sensor in physical connection with the flexible mat.

Preferably the first bounce location, the second bounce location, and/or the third bounce location is/are determined by at least one visual sensor directed toward the flexible mat.

Preferably the first bounce location, the second bounce location, and/or the third bounce location is/are determined by at least one device in physical connection with the user.

In a further aspect the invention comprises a system comprising a display configured to display a representation of a bounce instruction to a person on a flexible mat of a trampoline; and at least one processor in communication with the display, the processor configured to: receive a first bounce location of the person on the flexible mat; cause, to be displayed on the display, a representation of a bounce instruction to the person on the flexible mat; receive a second bounce location of the person on the flexible mat; responsive to determining a time of display of the bounce instruction prior to a lead time boundary interval, compare the second bounce location with the bounce instruction; and responsive to determining a time of display of the bounce instruction within the lead time boundary interval, receive a third bounce location and compare the third bounce location with the bounce instruction.

Preferably the bounce instruction comprises a bounce location instruction.

Preferably the representation of the bounce instruction comprises two or more bounce location targets, at least one of the bounce location targets presented so as to draw the attention of the user in order to present a bounce instruction to the user.

Preferably the representation of the bounce instruction comprises a virtual environment and at least one bounce location target within the virtual environment.

Preferably the bounce instruction comprises a bounce time interval instruction.

Preferably the bounce instruction comprises a bounce location instruction and a bounce time interval instruction.

Preferably the bounce time interval instruction comprises an instruction for the user to contact the flexible mat during a time interval.

Preferably the bounce time interval instruction comprises an instruction for the user to avoid contact with the flexible mat during a time interval.

Preferably the first bounce location, the second bounce location, and/or the third bounce location is/are determined by at least one sensor in physical connection with the flexible mat.

Preferably the first bounce location, the second bounce location, and/or the third bounce location is/are determined by at least one visual sensor directed toward the flexible mat.

Preferably the first bounce location, the second bounce location, and/or the third bounce location is/are determined by at least one device in physical connection with the user.

In a further aspect the invention comprises a computer readable medium on which is stored processor-executable instructions that, when executed by a processor, cause the processor to perform the methods described herein.

Preferably the processor-executable instructions comprise an application programming interface.

Preferably the processor-executable instructions comprise graphical user interface.

The term "connected to" includes all direct or indirect types of communication, including wired and wireless, via a cellular network, via a data bus, or any other computer structure. It is envisaged that they may be intervening elements between the connected integers. Variants such as "in communication with", "joined to", and "attached to" are to be interpreted in a similar manner.

The term "computer-readable medium" should be taken to include a single medium or multiple media. Examples of multiple media include a centralised or distributed database and/or associated caches. These multiple media store the one or more sets of computer executable instructions. The term "computer readable medium" should also be taken to include any medium that is capable of storing, encoding or carrying a set of instructions for execution by a processor and that cause the processor to perform any one or more of the methods described above. The computer-readable medium is also capable of storing, encoding or carrying data structures used by or associated with these sets of instructions. The term "computer-readable medium" includes solid-state memories, optical media and magnetic media.

The invention in one aspect comprises several steps. The relation of one or more of such steps with respect to each of the others, the apparatus embodying features of construction, and combinations of elements and arrangement of parts that are adapted to affect such steps, are all exemplified in the following detailed disclosure.

This invention may also be said broadly to consist in the parts, elements and features referred to or indicated in the specification of the application, individually or collectively, and any or all combinations of any two or more said parts, elements or features, and where specific integers are mentioned herein which have known equivalents in the art to which this invention relates, such known equivalents are deemed to be incorporated herein as if individually set forth.

In addition, where features or aspects of the invention are described in terms of Markush groups, those persons skilled in the art will appreciate that the invention is also thereby described in terms of any individual member or subgroup of members of the Markush group.

As used herein, '(s)' following a noun means the plural and/or singular forms of the noun.

As used herein, the term 'and/or' means 'and' or 'or' or both.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9, and 10) and also any range of rational numbers within that range (for example, 2 to 8, 1.5 to 5.5, and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

In this specification where reference has been made to patent specifications, other external documents, or other sources of information, this is generally for the purpose of providing a context for discussing the features of the invention. Unless specifically stated otherwise, reference to such external documents or such sources of information is not to be construed as an admission that such documents or such sources of information, in any jurisdiction, are prior art or form part of the common general knowledge in the art.

Although the present invention is broadly as defined above, those persons skilled in the art will appreciate that the invention is not limited thereto and that the invention also includes embodiments of which the following description gives examples.

BRIEF DESCRIPTION OF THE DRAWINGS

Preferred forms of the techniques for interpreting activity on a flexible mat of the trampoline and associated apparatus are described with reference to the accompanying drawings by way of example and without intending to be limiting, wherein:

FIG. 3 shows a preferred form jump cycle associated with a person bouncing on the flexible mat of FIG. 1;

DETAILED DESCRIPTION OF PREFERRED FORMS

Figure 1:
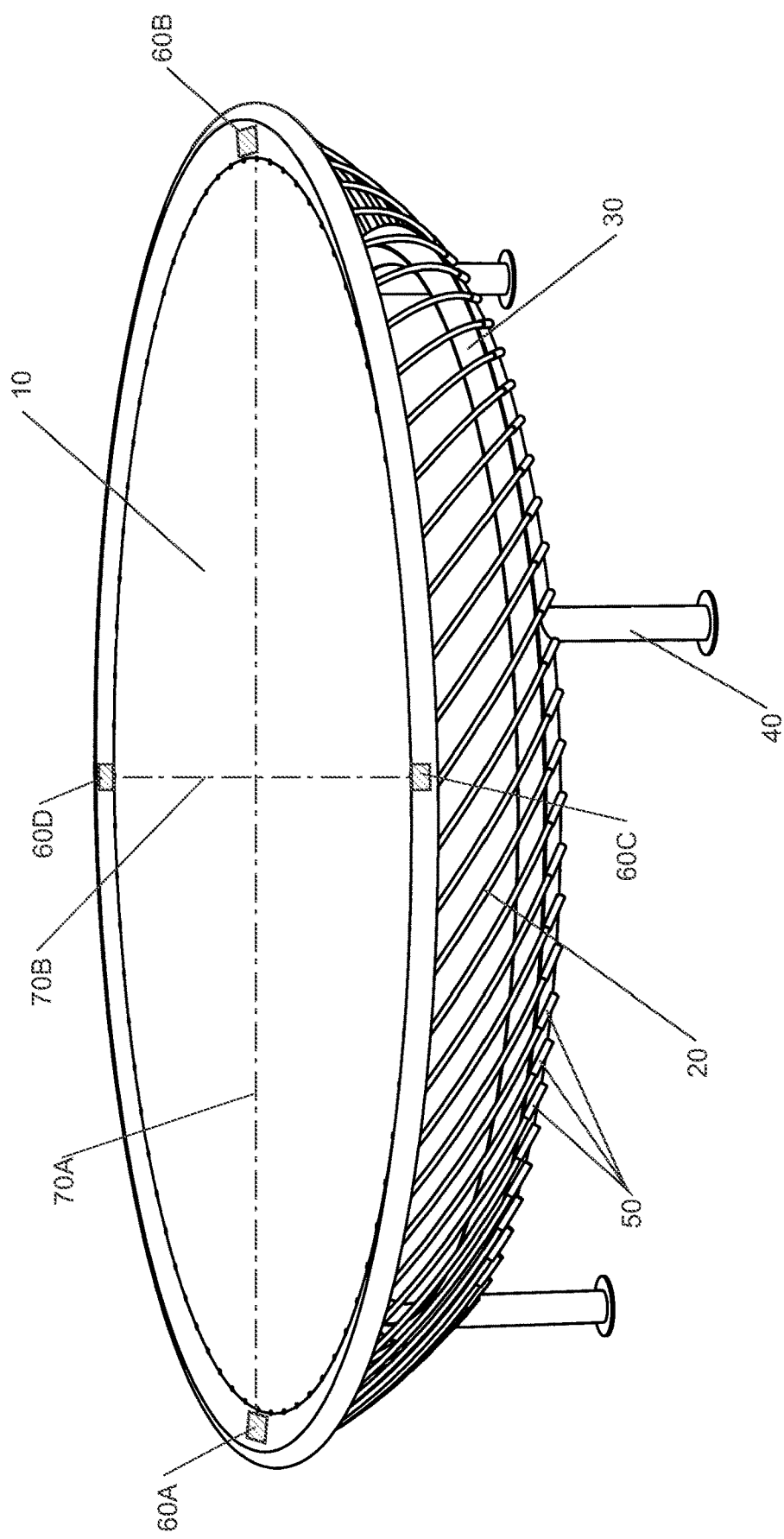
FIG. 1 is a perspective view of a preferred form trampoline for which a bounce location is desired.

FIG. 1 shows a preferred form trampoline in relation to which activity is interpreted. The preferred form trampoline comprises a flexible mat 10 on which a person may bounce, cause an object to bounce, or both. The trampoline further comprises a plurality of resiliently flexible rods 20 and a base frame that includes a circular beam 30 typically formed of steel or aluminum and supported from the ground by legs 40.

The rods 20 are typically fibreglass rods but may alternatively be formed of spring steel for example. The lower ends of the rods are retained by the circular beam 30. The upper ends of the rods connected to fittings as will be further described below. These fittings are coupled to the mat 10 about the periphery of the mat.

In a preferred form the lower ends of the rods 20 enter into tubular holders 50 fixed to the circular beam 30 as shown. Alternatively the lower ends of the rods are coupled to the circular beam 30 or a base frame of the trampoline of any other form.

The preferred form trampoline includes a sensor arrangement. The sensor arrangement comprises at least one sensor. As shown in FIG. 1, a preferred form sensor arrangement comprises two pairs of accelerometers. These accelerometers are shown at 60A, 60B, 60C and 60D. The four sensors 60 are shown as two pairs of sensors arranged around the mat. One pair of sensors 60A and 60B define an axis 70A across the mat. Sensors 60C and 60D define an axis 70B across the mat. As shown in FIG. 1, where there are two pairs of sensors, the pairs of sensors define orthogonal axes across the flexible mat 10.

In an embodiment the preferred form sensor arrangement comprises three or more sensors. In this embodiment the sensors are not necessarily provided as pairs of sensors arranged around the mat.

The sensor or sensors 60 are configured to measure a value corresponding to a deformation of the mat 10 as a person or object moves on or otherwise interacts with the mat. The value measured by the sensor(s) 60 corresponds to a proximity of the person or object to the sensor(s).

The term 'deformation' as used in this specification and claims in relation to a mat deformation signal or value includes displacement, velocity and/or acceleration of the mat edge.

It is envisaged that there are several suitable techniques for fixedly or removably mounting the sensors 60 in association with the trampoline. These techniques are described in PCT patent specification WO 2014/098628 and Australian Innovation patent 2013101110 for example.

Indicating Activity on the Mat

Figure 2:
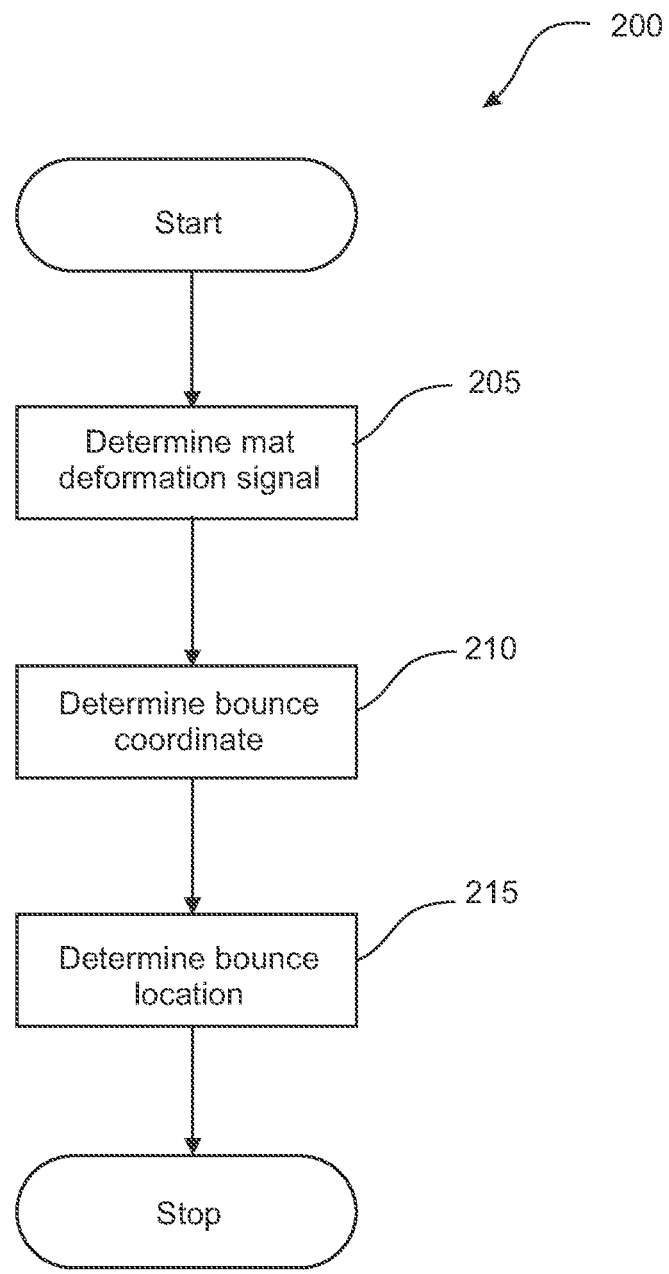
FIG. 2 shows a preferred form method for indicating activity of a person or object on the mat of a trampoline such as the trampolines of FIG. 1.

FIG. 2 shows at 200 a preferred form technique for indicating activity of a person or object on the mat. The method is directed toward determining a bounce location of a person on the mat 10.

As a person bounces on the flexible mat 10, the force exerted on the flexible mat is detected by the sensors 60 forming part of the sensor arrangement. The method includes the step of determining 205 a mat deformation signal.

In one preferred embodiment the signal includes data representing impact time and departure time that are then used for calculating the time of flight and for estimating bounce height. The impact time and the departure time define a bounce interval. Within the bounce interval is an interval of interest.

Once the mat deformation signal has been determined, the technique includes the step of determining 210 a bounce coordinate. The preferred form technique comprises calculating the sum of squared sample values for each of the sensors 60 during at least part of the interval of interest.

Once the bounce coordinate in a coordinate space has been determined, the technique includes the step of determining 215 a bounce location.

One or more bounce locations is associated with one or more regions on the flexible mat 10. There is stored a plurality of 'trained' positions. These trained positions represent average bounce coordinate readings recorded from a plurality of bounces on a single location on the flexible mat 10. A bounce location on the flexible mat is identified by finding the closest trained location.

In some cases an actual bounce location could be close to more than one bounce coordinate. Disambiguation techniques are applied to such bounce locations. One preferred form technique involves storing a truth table of possible ambiguous results and a bounce location that should be used in each circumstance.

Further techniques for determining bounce locations are described in PCT patent specification WO 2014/098628 and in Australian Innovation patent 2013101110 for example.

It is envisaged that there are several possible techniques, in addition to the techniques described above, for measuring and interpreting an activity of a person and/or for determining a bounce location of the person on the flexible mat.

In some examples, the flexible mat includes, or has placed upon it, sensors to assist in determining a bounce location of the person. In these examples the sensors are in physical connection with the flexible mat, the rods, or other components of the trampoline.

One example of such sensors involves pressure sensitive buttons stitched into the flexible mat. The locations of one or more of the buttons is known. As the person jumps on the flexible mat the person contacts one or more of the buttons. The location of the person on the flexible mat is determined by the button or buttons contacted by the person.

In another example the sensors involve a grid of conductive elastic threads suspended underneath the flexible mat such that the orthogonal directions are separated. As a person moves on the flexible mat, the threads are pressed together to complete a circuit which can be used to give a location.

A further example involves measuring the stress of the flexible rods 20 shown in FIG. 1 entering the frame of the trampoline at various locations. A location can be determined based on relative stresses of different parts of the frame.

In a further example, gyroscopes measure the change in angle of the edge of the flexible mat. Opposing angles are compared to determine the bounce location. In a further example the sensors involve grids of conductive thread stitched into the mat such that the intercepts do not touch. The person on the flexible mat wears conductive footwear such that their activity completes a circuit to give location.

A further example involves capacitive measurement of the surface of the flexible mat. The measurement detects the coupling of the person on the surface to locate a bounce.

In yet another example, pressure sensors included within the flexible rods 20 of FIG. 1 measure the deflection as a change in volume inside the rods.

In other examples, visual sensors are directed toward the flexible mat and/or the user on the flexible mat.

In one example an array of lasers is directed underneath the flexible mat across two axes to an array of photodiodes. Once two orthogonal beams are broken by an activity of a person, it is possible to determine an (x,y) location coordinate on the flexible mat.

In another example an array of infrared (IR) LEDs each transmit a different signal. A processor scans through the LEDs at a high frequency such that there is only ever one LED transmitting at a time. When an expected signal isn't received by a matching photodiode at the opposite side of the trampoline, it is assume that the beam has broken by a person crossing it, and an (x,y) location coordinate on the flexible mat can be determined.

In a further example a stereo camera measures the depth and location of the person on the flexible mat relative to the camera's position. Alternatively, orthogonal cameras are positioned to determine the location of maximum mat deflection underneath the edge of the flexible mat.

In a further example, sonar sensors are placed on the ground underneath the trampoline looking for the sensor with the lowest distance to the flexible mat.

In a further example a second person watches a person jumping on the flexible mat. The second person determines by visual inspection a bounce location of the person on the flexible mat.

Another example involves multiple sonar sensors placed at the edge of trampoline measuring the distance to the person on the flexible mat.

In other examples the person on the flexible mat is provided with devices to assist in determining a bounce location of the person. The devices are in physical connection with the user.

One such example device includes a Piksi GPS unit attached to the person to locate bounces.

In another example the person is attached to multiple recoiling cables. A rotary encoder is attached to the edge of the trampoline. The location of the person on the flexible mat is determined by a difference between encoders.

FIG. 3 shows a preferred form jump cycle associated with a person bouncing on the flexible mat 10.

Impact time is shown at 300. The impact time is the time when the person first contacts the flexible mat 10.

At point 310 the user remains in contact with the flexible mat 10. The force exerted on the flexible mat is caused by the person's weight while standing stationary on the mat.

Point 320 represents a point at the nadir of the person's bounce on the flexible mat 10.

At point 330 the force on the flexible mat 10 is once again equivalent to the person standing stationary on the mat. At point 330 the person is travelling upward, but still exerting a force on the mat.

Departure time 340 shows the user on an upward bounce leaving the flexible mat 10.

Airborne time 350 is the time during which the user is not in contact with the flexible mat 10. Following a period of being airborne, the user once again contacts the mat at an impact time shown at 300.

Figure 4:
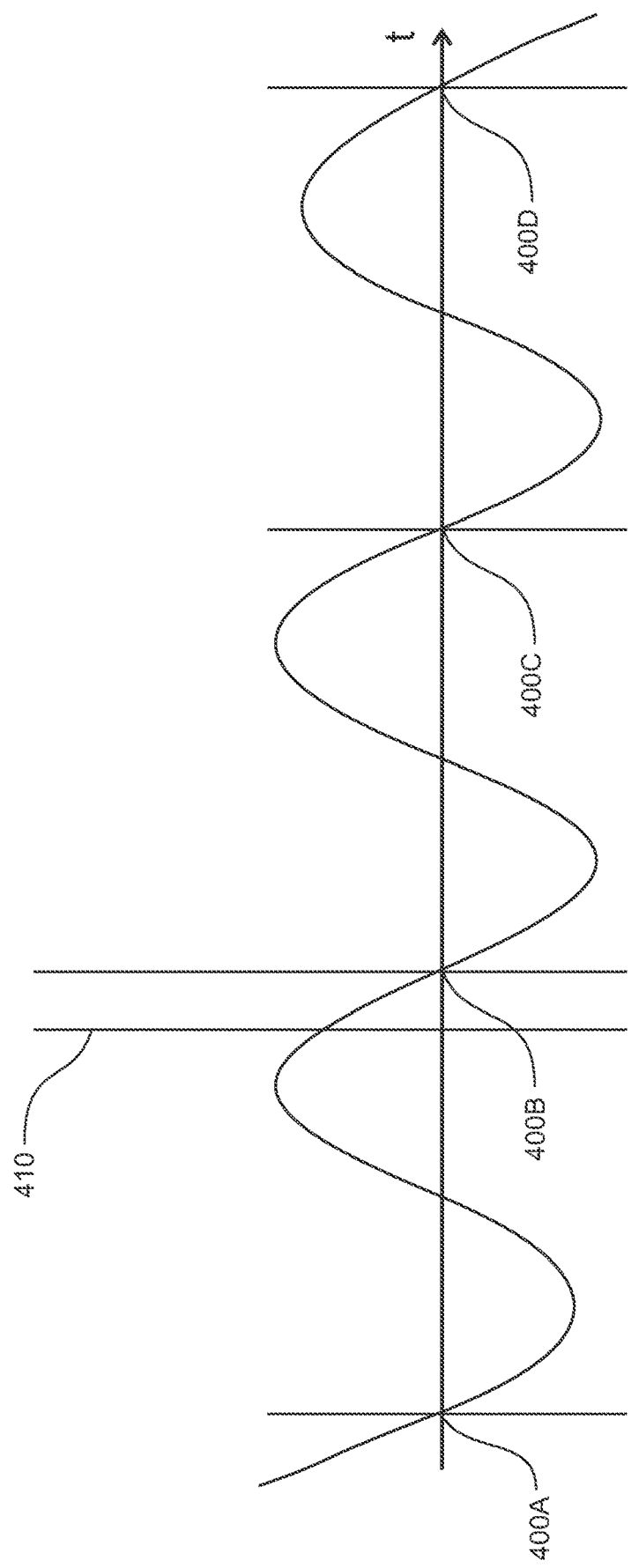
FIG. 4 shows a representation depicting four jump impact cycles.

FIG. 4 shows a graph depicting four jump impact cycles. Impact times are indicated at 400A, 400B, 400C and 400D. The graph also shows a time value 410 preceding impact time 400B. Time value 400B and time value 410 define a lead time boundary interval.

As will be described below, the user is provided with at least one and preferably a plurality of bounce instructions. A bounce instruction includes a bounce location instruction, a bounce time interval instruction, or a combination of a bounce location instruction and a bounce time interval instruction.

If a user is to be given a bounce instruction for impact time 400C, the bounce instruction is required to be provided to the user prior to time value 410. If the bounce instruction is issued before the user passes through the lead time boundary interval, then the user has enough time to orient their centre of mass at the departure following impact time 400B to aim for a target specified in the bounce instruction at impact time 400C.

On the other hand, if a user has already entered this boundary at impact time 400B, the user does not have sufficient time to orient their centre of mass to carry out the bounce instruction for impact time 400C. If a bounce instruction is provided after time value 410, the user has already entered the lead time boundary interval.

The bounce at impact time 400C is preferably recognised as a bounce that is not in response to the bounce instruction. The bounce is instead preferably interpreted as a "wait state" jump. The next bounce at impact time 400D is instead interpreted as carrying out the bounce instruction.

If a bounce instruction occurs after time value 410 then it is not possible for the jumper to hit the target at time 400C as a result of the given bounce instruction. If the bounce instruction occurs after time value 400B it is clear that the end of the lead time boundary interval has been reached. The lead time boundary is defined by time values 410 and 400B.

If a bounce instruction occurs between 410 and 400B then it is known that the target is not able to be hit as a result of the instruction, and if it is hit then it is by fluke. Preferably the jumper is not penalised for not hitting the target either.

The bounce instruction for example, could be presented for an additional jump cycle to give the player a legitimate opportunity to hit the target. Alternatively the bounce instruction is removed immediately before the jumper has an opportunity to follow it, and a new target for the next bounce cycle presented to a jumper.

Figure 5:
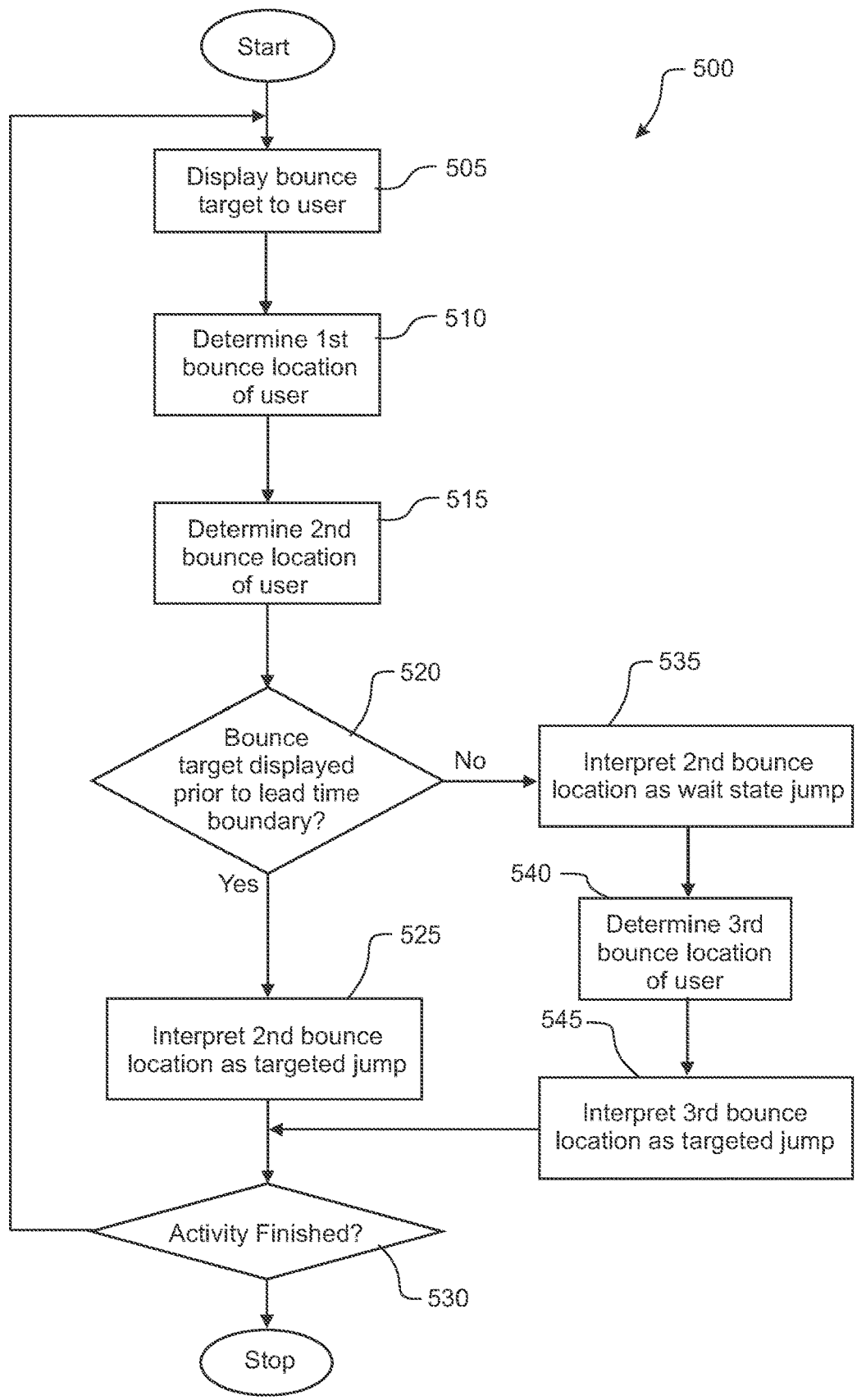
FIG. 5 shows a preferred form technique for interpreting activity of a person on the flexible mat 10 of the preferred form trampoline of FIG. 1.

FIG. 5 shows a preferred form technique for interpreting activity of a person on the flexible mat 10 of the preferred form trampoline of FIG. 1. The preferred form method 500 displays 505 a bounce target to a user.

In one embodiment the bounce target is a single target. In another embodiment there are multiple targets displayed one after the other to the user. In a further embodiment there are multiple targets, some of which are displayed to the user simultaneously.

After the bounce target has been displayed to the user, the technique determines 510 a first bounce location of the user. The first bounce location is determined for example by using the techniques described above. The first bounce location occurs at impact time 400B shown in FIG. 4.

The technique then determines 515 a second bounce location of the user. The second bounce location is determined preferably by using the same techniques described above for the first bounce location. Alternatively the second bounce location is determined by using a different technique to the first bounce location. The second bounce occurs at an impact time 400C shown in FIG. 4.

If 520 the bounce target was displayed prior to the lead time boundary shown in FIG. 4, then it is assumed that the user has been provided with sufficient time to attempt to meet the displayed bounce target. In this case the second bounce location is interpreted 525 as the targeted jump intended to meet the displayed bounce target.

If 530 the activity has finished the method stops. This would be the case for example where the user has complied with the last bounce target in a sequence of bounce targets, or has attempted a single bounce target where only one is presented.

If the activity has not yet finished control returns to step 505 where a further bounce target is displayed to the user.

If the bounce target has not been displayed with sufficient notice to the user, the second bounce location is interpreted 535 as a 'wait state jump'. This wait state jump occurs at impact time 400C. There is a recognition that the user has not been given sufficient time to meet a bounce target and is instead performing an interim jump before attempting the bounce target.

The third bounce location is determined 540. This bounce location occurs at impact time 400D.

The third bounce location is then interpreted 545 as the targeted jump in response to the bounce target displayed to the user.

Control then passes to check at step 530 whether the activity has finished.

Figure 6:
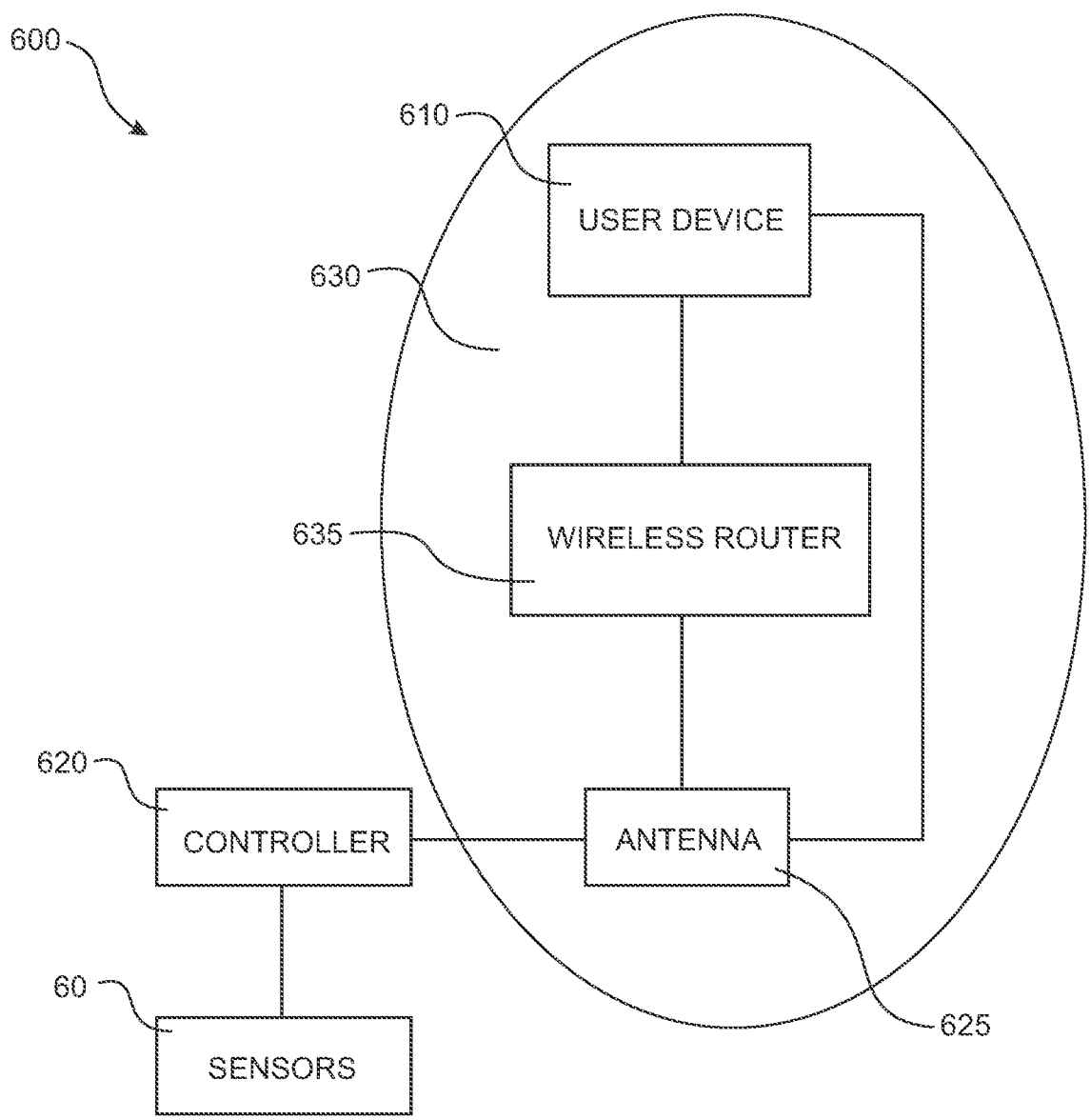
FIG. 6 shows a schematic diagram of a preferred form system for transferring data between the sensors of FIG. 1 and a user device.

FIG. 6 shows a schematic diagram of a preferred form system 600 for transferring data between the sensors 60 and a user device 610. Preferably the sensors are able to communicate either directly or indirectly with user device 610 over a wireless network, a wired network, or a combination of wireless and wired networks.

The sensors 60 are connected to a controller 620 configured to interpret signals from the sensors 60 and determine bounce locations using for example the techniques described above. Controller 620 includes or is connected to antenna 625. The antenna in turn is configured to establish a wireless data connection with user device 610.

In an embodiment, the antenna 625 establishes a connection with user device 610 directly using Bluetooth pairing or Wi-Fi Direct. In another embodiment the antenna 625 establishes a connection with user device 610 through a traditional wireless network 630 established by wireless router 635.

As the user jumps or bounces on the flexible mat 10 the bounce zones identified by the techniques described above are passed through an application programming interface (API) as input to the user device 610.

Referring to FIG. 3 and FIG. 6, in an embodiment the API provides one or more of the following data items to the user device 610 at bounce impact 300:

Notification that an impact has happened;
Number of bounces since controller 620 was activated;
Height of the previous bounce;
Time spent in the air in the previous bounce.

The controller 620 determines the bounce location of the user between the time of user impact 300 and user departure 340. In an embodiment the controller 620 determines the bounce location shortly before user departure 340, or at least closer to user departure 340 than user impact 300.

Once the controller 620 determines user bounce location the API provides to the user device 610 a representation of bounce location. One example format includes the location in polar coordinates relative to the centre of the trampoline.

At bounce departure 340 in an embodiment the API provides one or more of the following data items to the user device 610:

Notification that the user has departed the mat;
Time spent on the mat during user bounce.

An application running on user device 610 initialises controller 620 by specifying which data the application wishes to receive. The controller 620 then responds with event packets as they occur.

Figure 7:
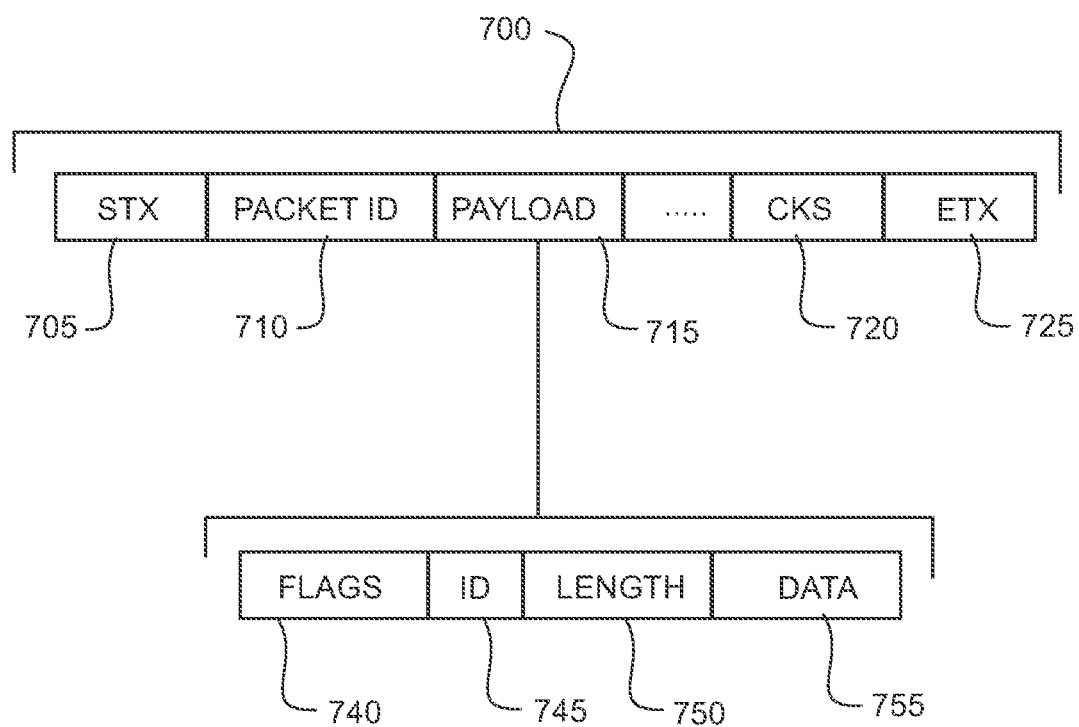
FIG. 7 shows a preferred form packet of data sent between the controller and user device of FIG. 6.

FIG. 7 shows a preferred form packet 700 of data. Data packet 700 is transmitted in a serial stream. A typical packet includes start byte STX 705, a one byte packet ID number 710, at least one payload 715 of variable length, a one byte checksum CKS 720, and a stop byte ETX 725. All data packets preferably start with STX 705 and end with ETX 725.

In an embodiment the data packets 700 sent from the controller 620 to the user device 610 use even packet ID numbers 710. Data packets 700 sent from the user device 610 to the controller 620 use odd packet ID numbers 710. In another embodiment data packets sent from the controller use odd packet ID numbers and data packets sent from the user device 610 use even packet ID numbers.

Preferably the packet ID numbers 710 increase sequentially.

The payload 715 preferably comprises a one byte bit-array of flags 740, a one byte payload ID 745, a one byte data length 750 and the corresponding data 755.

Examples of flags include indicators of one or more of the following:
whether the payload 715 has length
whether the payload comprises a negative acknowledgement.

The payload ID 745 is a unique identification number that indicates the purpose and format of the data 755 contained in the payload 715.

The length 750 represents the size of the payload data 755 in bytes. Preferably the length excludes the checksum CKS 720, and header/packet delimiters.

The payload data 755 is specific to the payload type being sent. Generally the payload data comprises an unsigned integer type unless explicitly specified otherwise.

The checksum CKS 720 comprises a simple CRC-8 bit type. The checksum covers all bytes in the packet, excluding STX 705, CKS 720 and ETX 725.

In an embodiment all packets received by either the controller 620 or the user device 610 are responded to with an acknowledgement. The acknowledgement payload identifier is one greater than the payload identifier of the received packet being acknowledged.

Where a packet contains multiple payloads, acknowledgement for the entire packet preferably uses the payload identifier one greater than the first received payload in the packet.

The header of the acknowledgement packet includes a bit that specifies whether it is a positive or negative acknowledgement. In the case of success, the payload will be empty or contain the requested data in the format specified for that payload identifier. In the case of failure, the payload contains an 8 bit error code.

In an embodiment there are 4 distinct types of payload. These include:
request—a request for data sent from the user device 610 to the controller 620
response—a reply to a request sent from the controller 620 to the user device 610
command—an instruction or data sent from user device 610 to controller 620. Commands are replied to with an acknowledgement packet
event—a message or data triggered by some condition that is sent from the controller 620 to the user device 610. Events must be acknowledged, otherwise they will be retransmitted.

Preferred form requests include one or more of the following:
time since the controller was reset
how long trampoline jumper has been active for
how long the trampoline has been inactive for
cumulative time spent in the air since reset
total calories burned since reset
current battery charge status.

Requests for data sent from the user device 610 are replied to with a response from the controller 620. Time measurements are preferably represented in milliseconds Preferred form commands sent from the user device 610 to the controller 620 include commands to toggle which events are streamed to the user device 610. To enable an option, the user device 610 sends a non-zero payload. To disable an option the user device 610 sends an all-zero payload.

The controller 620 returns an acknowledgement packet of length 0 with an identifier one greater than the packet identifier of the received packet, with the acknowledgement bit set accordingly.

Preferred form commands include one or more of the following:
instruct the controller 620 to reset
select which trampoline model is being used
inform the controller 620 which direction is designated as 'forward'
instruct the controller whether or not to stream bounce data events
milliseconds the trampoline has to be inactive to be considered passive The events for which commands are used to toggle include one or more of the following:
when the jumper contacts trampoline
when the jumper leaves contact with the trampoline
bounce height in millimetres
time spent in the air in milliseconds
time spent on the trampoline mat in milliseconds
bounce number since reset
bounce number and current activity
notification of activity on the trampoline
notification of lack of activity on the trampoline
calories burned in the previous bounce
polar coordinates.

An event is typically reported from the controller 620 to the user device 610 as soon as the event occurs. Preferably an event is only sent if the option has been enabled beforehand. Preferably the events are grouped together into sets that are attributed to the same phase in the trampoline bounce. They are sent to the user device 610 in a single grouped packet.

Typical events include one or more of the following:
controller 620 detects a landing on the trampoline mat
number of bounces completed since reset
number of bounces completed in the current period of activity
bounce height in millimetres reported at impact
bounce airtime in milliseconds reported at impact
calories burned on previous bounce
polar coordinates
detected bounce location
controller detects departure from the trampoline mat
the time in milliseconds spent on the mat between bounces reported at departure
instance when trampoline becomes active
instance when trampoline is no longer active
alert when battery is getting low Preferably the user device 610 includes at least a processor, a display, and a user input facility. The user input facility includes for example a touch screen on the device 610 and the inputs specified as bounce zones from the user on the flexible mat 10.

The user device 610 operates under application specific software that takes as input data representing the bounce zones or locations or other measured activity from the user and uses these inputs to provide information and/or entertainment to a user viewing the handheld device 610.

The device 610 in combination with the trampoline embodiments described above provide apparatus relating to gaming, communication, rehabilitation and the like.

Preferably it is the application controlling the device 610 that determines the function of the apparatus. In each case the device provides interaction with the user based at least partly on the activity of the user or an object on the flexible mat.

Figure 8:
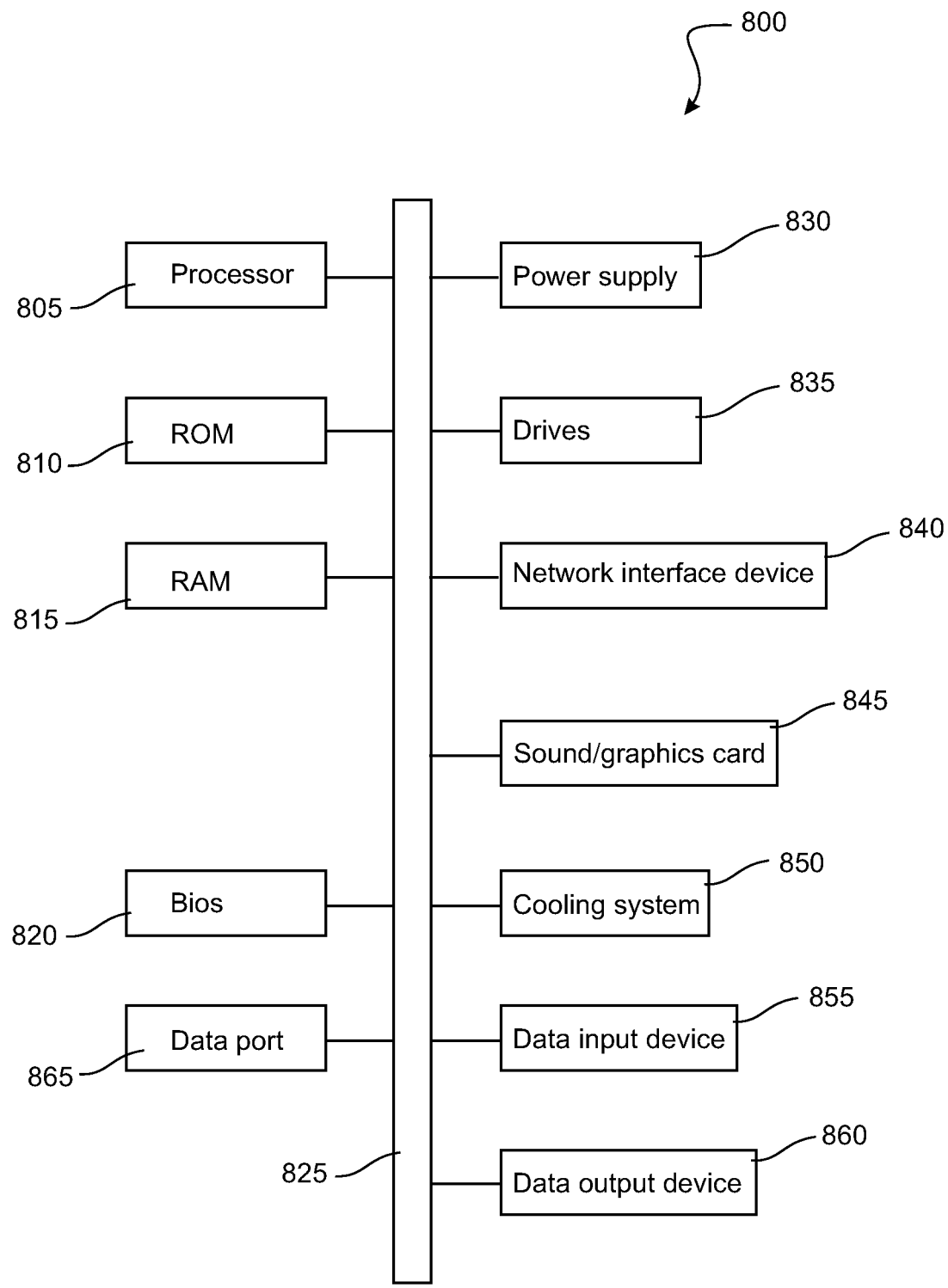
FIG. 8 shows a simplified block diagram of a device forming at least part of the user device of FIG. 6.

FIG. 8 shows a simplified block diagram of a device forming at least part of user device 610 in the example form of a computing device 800.

Sets of computer executable instructions are executed within device 800 that cause the device 800 to perform the methods described above. Preferably the computing device 800 is connected to other devices. Where the device is networked to other devices, the device is configured to operate in the capacity of a server or a client machine in a server-client network environment. Alternatively the device can operate as a peer machine in a peer-to-peer or distributed network environment. The device may also include any other machine capable of executing a set of instructions that specify actions to be taken by that machine. These instructions can be sequential or otherwise.

A single device 800 is shown in FIG. 8. The term "computing device" also includes any collection of machines that individually or jointly execute a set or multiple sets of instructions to perform any one or more of the methods described above.

The example computing device 800 includes a processor 805. One example of a processor is a central processing unit or CPU. The device further includes read-only memory (ROM) 810 and random access memory (RAM) 815. Also included is a Basic Input/Output System (BIOS) chip 820. The processor 805, ROM 810, RAM 815 and the BIOS chip 820 communicate with each other via a central motherboard 825.

Computing device 800 further includes a power supply 830 which provides electricity to the computing device 800. Power supply 830 may also be supplemented with a rechargeable battery (not shown) that provides power to the device 800 in the absence of external power.

Also included are one or more drives 835. These drives include one or more hard drives and/or one or more solid state flash hard drives. Drives 835 also include optical drives.

Network interface device 840 includes a modem and/or wireless card that permits the computing device 800 to communicate with other devices. Computing device 800 may also comprise a sound and/or graphics card 845 to support the operation of the data output device 860 described below. Computing device 800 further includes a cooling system 850 for example a heat sink or fan.

Computing device 800 includes one or more data input devices 855. These devices include a keyboard, touchpad, touchscreen, mouse, and/or joystick. The device(s) take(s) input from manual keypresses, user touch with finger(s) or stylus, spoken commands, gestures, and/or movement/orientation of the device.

Data output device(s) 860 include(s) a display and/or printer. Device(s) 860 may further include computer executable instructions that cause the computing device 800 to generate a data file such as a PDF file.

Data port 865 is able to receive a computer readable medium on which is stored one or more sets of instructions and data structures, for example computer software. The software causes the computing device 800 to perform one or more of the methods or functions described above. Data port 865 includes a USB port, Firewire port, or other type of interface. The computer readable medium includes a solid state storage device. Where drives 835 include an optical media drive, the computer readable medium includes a CD-ROM, DVD-ROM, Blu-ray, or other optical medium.

Software may also reside completely or at least partially within ROM 810, within erasable non-volatile storage and/or within processor 805 during execution by the computing device 800. In this case ROM 810 and processor 805 constitute computer-readable tangible storage media. Software may further be transmitted or received over a network via network interface device 840. The data transfer uses any one of a number of well known transfer protocols. One example is hypertext transfer protocol (http).

Figure 9:
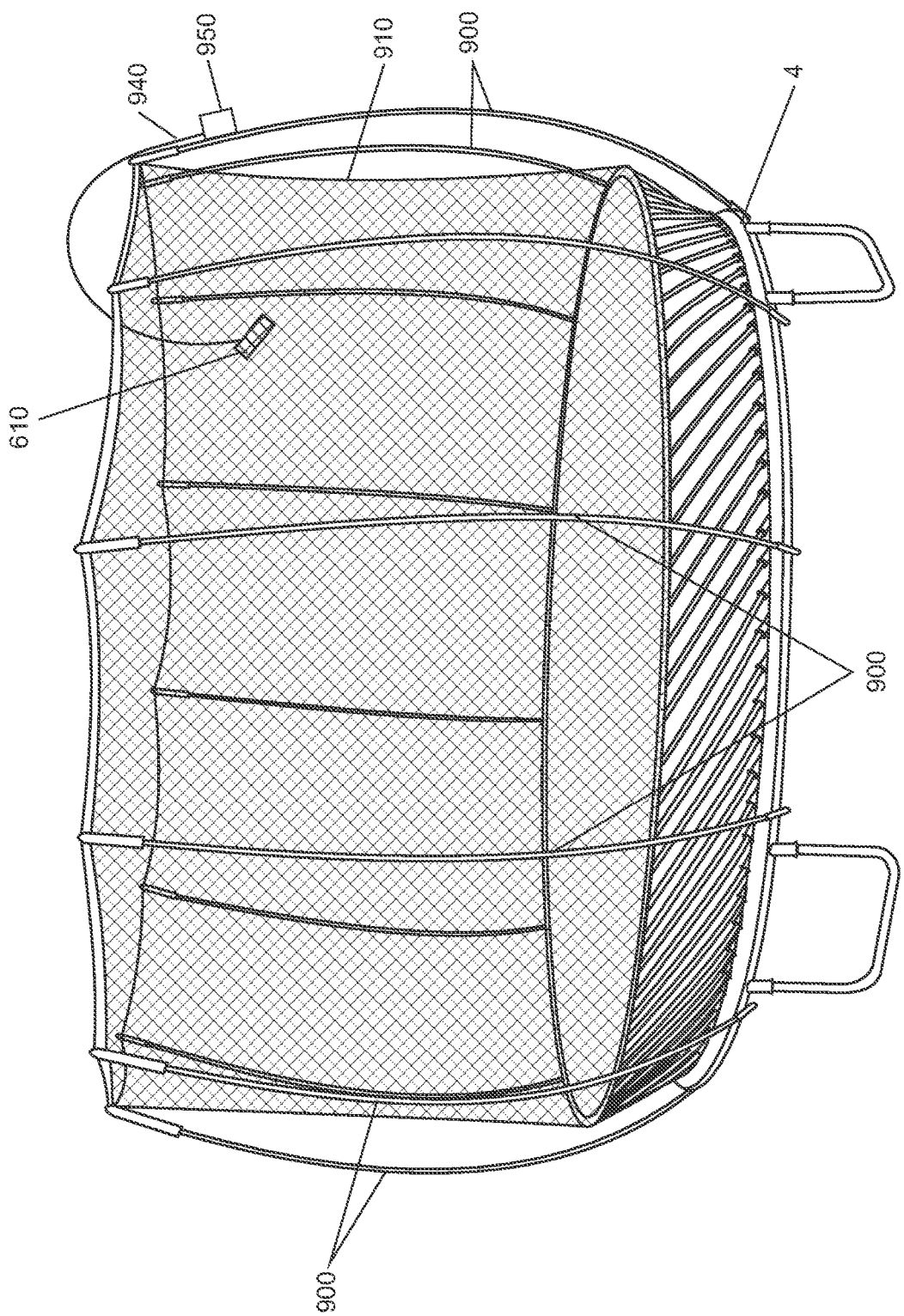
FIG. 9 shows a preferred form mounting arrangement for the handheld device of FIG. 6.

FIG. 9 shows a preferred form trampoline that includes an enclosure system. The enclosure system consists of a plurality of resiliently flexible generally upright enclosure support members 900 which in the preferred form are flexible or deformable fibreglass rods.

Enclosure support members 900 are referred to below as enclosure rods for convenience but it is to be understood that this term is non limiting in relation to the size and cross-sectional shape of the enclosure support elements and the material from which they are formed.

The preferred form enclosure system also comprises a barrier net 910. The enclosure rods 900 support the net 910 above the flexible mat. The lower edge of the barrier net 910 is coupled directly or indirectly to the peripheral edge of the mat. Barrier net 910 is typically formed of a lightweight but strong net material. Alternatively this could be a flexible fabric material which is for example opaque or which is perforated so as to be semi-opaque.

Preferred form enclosures are more particularly described in U.S. Pat. No. 7,708,667 and in PCT patent specification WO 2014/098628 for example.

Where there is an enclosure provided as shown in FIG. 9, there is preferably provided a mounting arrangement comprising a flexible rod 940. The flexible rod 940 is fixedly or removably mounted at point 950 to one or more of the enclosure rods 900. The flexible rod 940 is shaped and formed to enable a user to position at least part of the flexible rod 940 within the barrier net 910. Preferably the flexible rod 940 is constructed so that it can be manipulated and configured yet retain a shape desired by the user.

The flexible rod 940 is preferably provided with a mounting point to enable user device 610 to be removably attached and supported by the flexible rod 940. In an alternative embodiment the mounting point includes a dock adapted to establish a physical connection with user device 610, providing power and/or data connectivity to device 610.

The mounting point 950 is preferably configured to pivot to enable a wide range of positions and angles for the user device 610. Alternatively the flexible rod 940 is sufficiently flexible to permit a selection of various angles. In each case the user device 610 is positioned to allow a user to interact with it, for example by touching with a finger or stylus to operate the user interface of the device 610.

In an alternative embodiment the mounting arrangement is fixedly or removably mounted to the barrier net 910. The mounting arrangement is constructed to enable user device 610 to be removably attached to the mounting arrangement so that in use the handheld device is supported in a position inside or outside the barrier net 910.

Alternatively the mounting arrangement otherwise suspends the handheld device inside or outside the barrier net 910.

It will be appreciated that the mounting arrangement comprising the flexible rod 940 could also include a shower proof hood or sunshade to protect the user device 610 and/or to make the display more visible to the user. It will be appreciated that the display could also include a projector able to take input from the user device 610 and to project an image or display on to a surface.

Figure 10:
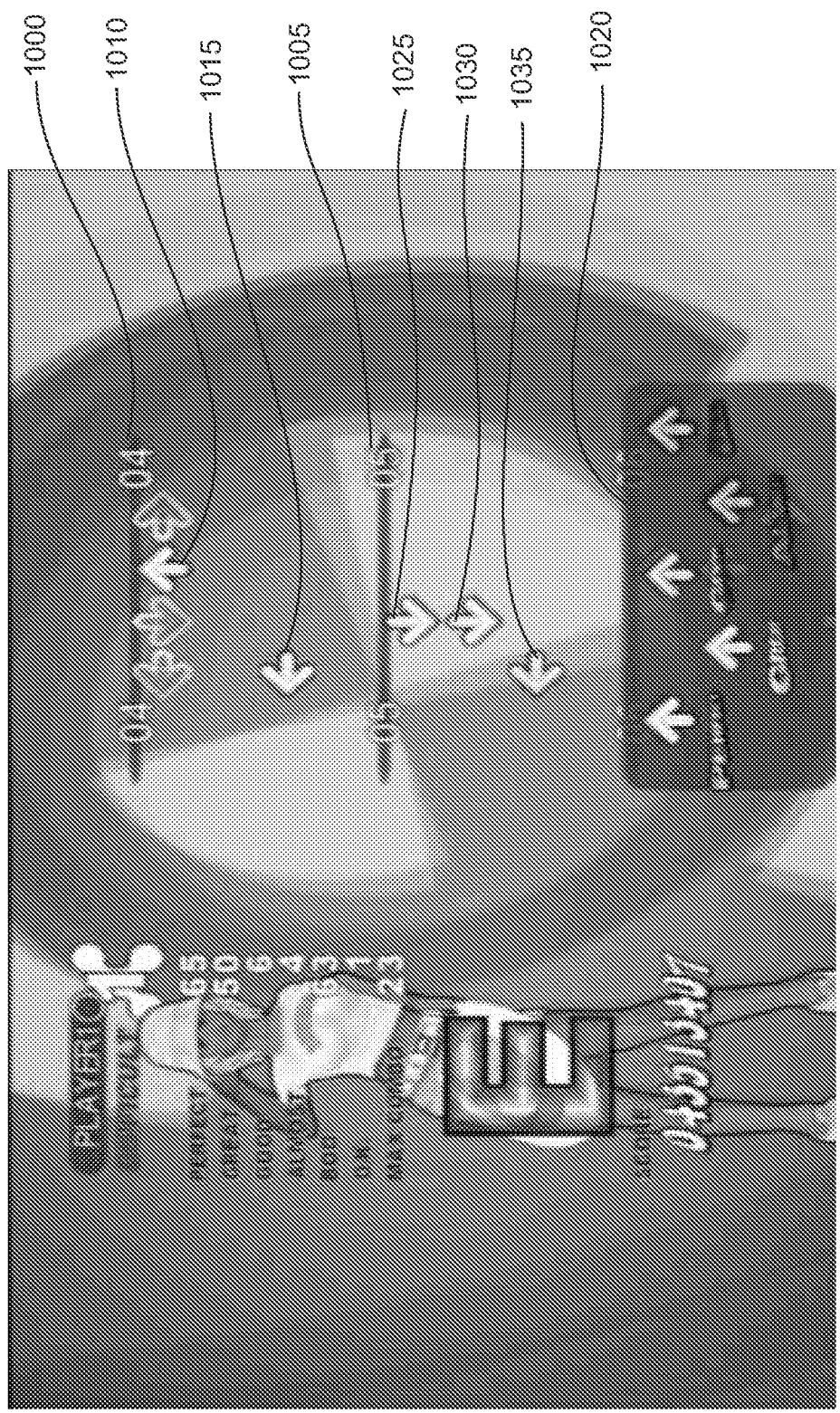
FIG. 10 shows an example of a game that presents one or more targets to a user.

FIG. 10 shows a graphical user interface in the form of a game that presents one or more targets to a user. The display shows a time period 1000 and a time period 1005. Between the two time periods 1000 and 1005 the user is presented with bounce instruction 1010 requiring a jump to a forward position on the mat. Within the same time period the user is also presented with bounce instruction 1015 requiring a jump to a leftward position on the mat.

Bounce instruction 1010 is one of four bounce locations forming part of a representation of a bounce instruction. Bounce instruction 1010 is presented in a different colour so as to draw the attention of the user in order to present a bounce instruction target to the user.

It is anticipated that the user carry out bounce instruction 1010 prior to carrying out bounce instruction 1015. It is anticipated that there is an indicator of temporal order provided to the user. In FIG. 10 bounce instruction 1010 is displayed closer to time period 1000 than bounce instruction 1015. As time period 1000 occurs before time period 1005 this indicated to the user that bounce instruction 1010 should be carried out before bounce instruction 1015.

Bounce instructions 1010 and 1015 are only displayed within the time interval defined by time period 1000 and time period 1005. After time period 1005 the bounce instructions are no longer displayed, regardless of whether or not the user successfully carried out the bounce instruction.

Between time period 1005 and time period 1020 there are displayed three bounce instructions. Bounce instructions 1025 and 1030 require a jump to a rearward position on the mat. Bounce instruction 1035 requires a jump to a leftward position on the mat.

The required temporal order of bounce instructions 1025, 1030, and 1035 is indicated to the user in the same manner as that described above. Bounce instructions 1025, 1030, and 1035 are only displayed within the time interval defined by time period 1005 and time period 1020, regardless of whether or not the user successfully carried out the bounce instruction.

Figure 11:
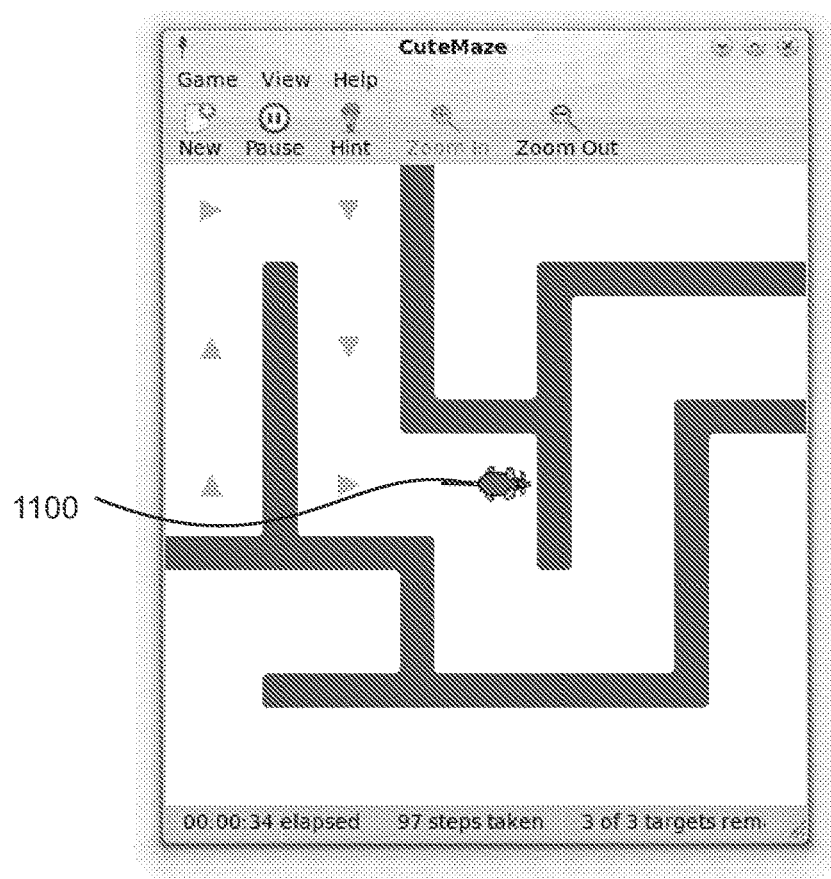
FIG. 11 shows an example of a game that presents multiple targets to a user.

FIG. 11 shows a graphical user interface in the form of a game that presents multiple targets to a user. The display shows an avatar 1100 within a virtual environment. In this case the virtual environment comprises a maze. The user is presented with a goal, which in the illustrated example, includes navigating through an environment. The user is presented with at least one bounce location target within the virtual environment.

The bounce instructions presented to a user vary according to the position of the user's avatar within the environment. For example the avatar 1100 is constrained from movement in two directions by obstacles such as walls. The user is presented with two alternative bounce instructions.

From the perspective of the user, the bounce instructions include leftward movement and downward movement. From the perspective of the user's avatar, the bounce instructions include backward movement or rightward movement.

Each time a user's avatar moves to a new position in the environment, a new set of alternative bounce instructions is presented to the user. In an embodiment the set of bounce instructions changes of time. For example an obstacle within the environment may appear or disappear. A desirable item may also appear or disappear.

Figure 12:
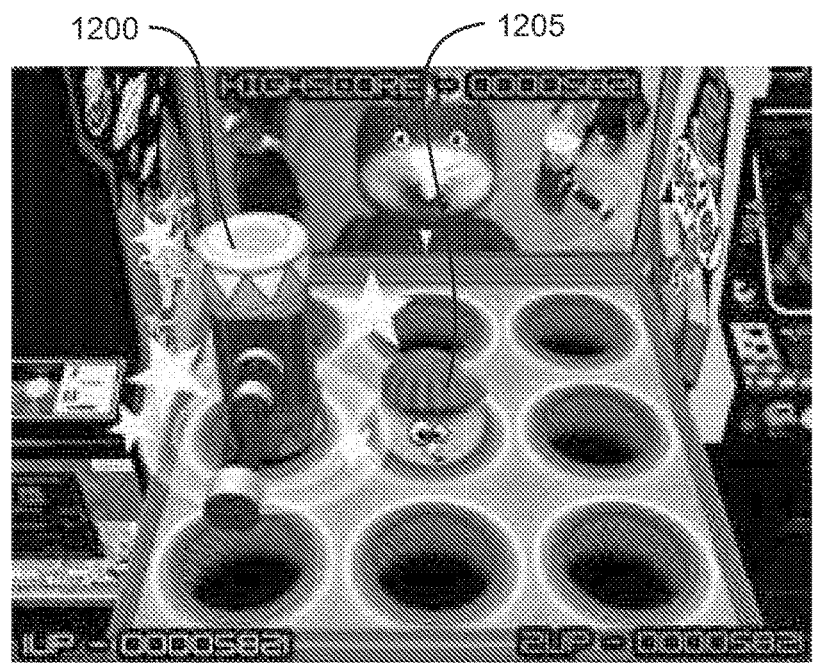
FIG. 12 shows an example of a game that presents multiple targets to a user.

FIG. 12 shows a graphical user interface in the form of a game that presents multiple targets to a user. The display shows a grid of nine possible bounce targets. The user has been presented with two concurrent bounce instructions, the bounce targets for which are indicated at 1200 and 1205 respectively. The bounce instructions are presented so as to draw the attention of the user in order to present at least one bounce instruction target. In this case, one or more objects to be hit are shown associated to respective bounce locations.

As shown in FIG. 12 the user has complied with the bounce instruction for bounce target 1200 but not the bounce instruction for bounce target 1205. The user has been presented with a choice of bounce targets and has made a selection.

A bounce instruction for bounce location 1200 is only displayed within a defined time interval. A bounce instruction for bounce location 1205 is also only displayed within a defined time interval. The time intervals for bounce locations 1200 and 1205 may overlap so that the bounce instructions are presented at the same time. Alternatively the time intervals for bounce locations 1200 and 1205 do not overlap so that the bounce instructions are not presented at the same time. The time intervals may be the same length, or may differ in length.

The foregoing describes the invention including preferred forms thereof. Modifications and improvements as would be obvious to those skilled in the art are intended to be incorporated in the scope hereof, as defined by the accompanying claims.

The invention claimed is:

1. A method of interpreting an activity of a person on a flexible mat of a trampoline, the method comprising:
    determining, by a processor, a bounce instruction for the person on the flexible mat;
    determining, by the processor, a first bounce location and a first bounce impact time of the person on the flexible mat based on a first signal from a sensor arrangement in physical connection with the flexible mat;

determining, by the processor, a second bounce location and a second bounce impact time of the person on the flexible mat based on a second signal from the sensor arrangement;

determining, by the processor, a lead time boundary interval, the lead time boundary interval defined by the first bounce impact time and a time value preceding the first bounce impact time and following an impact time of a bounce preceding the first bounce impact time;

displaying, by a display device, the bounce instruction to the person on the flexible mat; and determining, by the processor, a time of display of the bounce instruction to the person on the flexible mat;

wherein when the time of display of the bounce instruction is prior to the lead time boundary interval, the processor will compare the second bounce location with the bounce instruction, and wherein when the time of display of the bounce instruction is within the lead time boundary interval, the processor will determine a third bounce location and a third bounce impact time of the person on the flexible mat based on a third signal from the sensor arrangement and compare the third bounce location with the bounce instruction.

2. The method of claim 1, wherein the bounce instruction comprises a bounce location instruction.

3. The method of claim 2, wherein the bounce instruction comprises two or more bounce location targets, at least one of the bounce location targets presented in a different colour or as an object so as to draw the attention of the person on the flexible mat in order to present a bounce instruction target to the person on the flexible mat.

4. The method of claim 2, wherein the bounce instruction comprises a virtual environment and at least one bounce location target within the virtual environment.

5. The method of claim 1, wherein the bounce instruction comprises a bounce time interval instruction.

6. The method of claim 5, wherein the bounce time interval instruction comprises an instruction for the person on the flexible mat to contact the flexible mat during a time interval.

7. The method of claim 5, wherein the bounce time interval instruction comprises an instruction for the person on the flexible mat to avoid contact with the flexible mat during a time interval.

8. The method of claim 1, wherein the bounce instruction comprises a bounce location instruction and a bounce time interval instruction.

9. A method of instructing an activity of a person on a flexible mat of a trampoline, the method comprising:

determining, by a processor, to determine a bounce instruction for the person on the flexible mat;

displaying, by a display device, the bounce instruction to the person on the flexible mat;

determining, by the processor, a first bounce location and a first bounce impact time of the person on the flexible mat based on a first signal from a sensor arrangement in physical connection with the flexible mat;

determining, by the processor, a second bounce location and a second bounce impact time of the person on the flexible mat based on a second signal from the sensor arrangement;

determining, by the processor, a lead time boundary interval the lead time boundary interval defined by the first bounce impact time and a time value preceding the first bounce impact time and following an impact time of a bounce preceding the first bounce impact time; and determining, by the processor, a time of display of the bounce instruction to the person on the flexible mat;

wherein when the time of display of the bounce instruction is prior to the lead time boundary interval, the processor will compare the second bounce location with the bounce instruction, and wherein when the time of display of the bounce instruction is within the lead time boundary interval, the processor will determine a third bounce location and a third bounce impact time of the person on the flexible mat based on a third signal from the sensor arrangement and compare the third bounce location with the bounce instruction.

10. The method of claim 9, wherein the bounce instruction comprises a bounce location instruction.

11. The method of claim 10, wherein the bounce instruction comprises two or more bounce location targets, at least one of the bounce location targets presented in a different colour or as an object so as to draw the attention of the person on the flexible mat in order to present a bounce instruction to the person on the flexible mat.

12. The method of claim 10, wherein the bounce instruction comprises a virtual environment and at least one bounce location target within the virtual environment.

13. The method of claim 9, wherein the bounce instruction comprises a bounce time interval instruction.

14. The method of claim 13, wherein the bounce time interval instruction comprises an instruction for the person on the flexible mat to contact the flexible mat during a time interval.

15. The method of claim 13, wherein the bounce time interval instruction comprises an instruction for the person on the flexible mat to avoid contact with the flexible mat during a time interval.

16. The method of claim 9, wherein the bounce instruction comprises a bounce location instruction and a bounce time interval instruction.

17. A system comprising:

a sensor arrangement in physical connection with a flexible mat of a trampoline;

a display device; and a processor in communication with the sensor arrangement and the display device, said processor being configured to:

determine a bounce instruction for a person on the flexible mat of the trampoline;

determine a first bounce location and a first bounce impact time of the person on the flexible mat based on a first signal from the sensor arrangement;

determine a second bounce location and a second bounce impact time of the person on the flexible mat based on a second signal from the sensor arrangement;

determine a lead time boundary interval, the lead time boundary interval defined by the first bounce impact time and a time value preceding the first bounce impact time and following an impact time of a bounce preceding the first bounce impact time;

cause the display device to provide the bounce instruction to the person on the flexible mat; and determine a time of display of the bounce instruction to the person on the flexible mat;

wherein when the time of display of the bounce instruction is prior to the lead time boundary interval, the processor will compare the second bounce location with the bounce instruction, and wherein when the time of display of the bounce instruction is within the lead time boundary interval, the processor will determine a third bounce location and a third bounce impact time of the person on the flexible mat based on a third signal from the sensor arrangement and compare the third bounce location with the bounce instruction.

18. The system of claim 17, wherein the bounce instruction comprises a bounce location instruction.

19. The system of claim 18, wherein the bounce instruction comprises two or more bounce location targets, at least one of the bounce location targets presented in a different colour or as an object so as to draw the attention of the person on the flexible mat in order to present a bounce instruction target to the person on the flexible mat.

20. The system of claim 18, wherein the bounce instruction comprises a virtual environment and at least one bounce location target within the virtual environment.

21. The system of claim 17, wherein the bounce instruction comprises a bounce time interval instruction.

22. The system of claim 21, wherein the bounce time interval instruction comprises an instruction for the person on the flexible mat to contact the flexible mat during a time interval.

23. The system of claim 21, wherein the bounce time interval instruction comprises an instruction for the person on the flexible mat to avoid contact with the flexible mat during a time interval.

24. The system of claim 17, wherein the bounce instruction comprises a bounce location instruction and a bounce time interval instruction.

25. A system comprising:
a display device configured to provide a bounce instruction to a person on a flexible mat of a trampoline; and
a processor in communication with the display device, the processor configured to:
determine the bounce instruction for the person on the flexible mat;
determine a first bounce location and a first bounce impact time of the person on the flexible mat based on a first signal from a sensor arrangement in physical connection with the flexible mat;
determine a second bounce location and a second bounce impact time of the person on the flexible mat based on a second signal from the sensor arrangement;
determine a lead time boundary interval, the lead time boundary interval defined by the first bounce impact time and a time value preceding the first bounce impact time and following an impact time of a bounce preceding the first bounce impact time; and
determine a time of display of the bounce instruction to the person on the flexible mat;
wherein when the time of display of the bounce instruction is prior to the lead time boundary interval, the processor will compare the second bounce location with the bounce instruction, and
wherein when the time of display of the bounce instruction is within the lead time boundary interval, the processor will determine a third bounce location and a third bounce impact time of the person on the flexible mat based on a third signal from the sensor arrangement and compare the third bounce location with the bounce instruction.

26. The system of claim 25, wherein the bounce instruction comprises a bounce location instruction.

27. The system of claim 26, wherein the representation of the bounce instruction comprises two or more bounce location targets, at least one of the bounce location targets presented in a different colour or as an object so as to draw the attention of the person on the flexible mat in order to present a bounce instruction target to the person on the flexible mat.

28. The system of claim 26, wherein the bounce instruction comprises a virtual environment and at least one bounce location target within the virtual environment.

29. The system of claim 25, wherein the bounce instruction comprises a bounce time interval instruction.

30. The system of claim 29, wherein the bounce time interval instruction comprises an instruction for the person on the flexible mat to contact the flexible mat during a time interval.

31. The system of claim 29, wherein the bounce time interval instruction comprises an instruction for the person on the flexible mat to avoid contact with the flexible mat during a time interval.

32. The system of claim 25, wherein the bounce instruction comprises a bounce location instruction and a bounce time interval instruction.

33. A computer readable medium on which is stored processor-executable instructions that, when executed by a processor, cause the processor to perform a method of interpreting an activity of a person on a flexible mat of a trampoline, the method comprising:
determining, by the processor, a bounce instruction for the person on the flexible mat;
determining, by the processor, a first bounce location and a first bounce impact time of the person on the flexible mat based on a first signal from a sensor arrangement in physical connection with the flexible mat;
determining, by the processor, a second bounce location and a second bounce impact time of the person on the flexible mat based on a second signal from the sensor arrangement;
determining, by the processor, a lead time boundary interval, the lead time boundary interval defined by the first bounce impact time and a time value preceding the first bounce impact time and following an impact time of a bounce preceding the first bounce impact time;
displaying, by a display device, the bounce instruction to the person on the flexible mat; and
determining, by the processor, a time of display of the bounce instruction to the person on the flexible mat;
wherein when the time of display of the bounce instruction is prior to the lead time boundary interval, the processor will compare the second bounce location with the bounce instruction, and
wherein when the time of display of the bounce instruction is within the lead time boundary interval, the processor will determine a third bounce location and a third bounce impact time of the person on the flexible mat based on a third signal from the sensor arrangement and compare the third bounce location with the bounce instruction.

34. The computer readable medium of claim 33, wherein the processor-executable instructions comprise an application programming interface.

35. The computer readable medium of claim 33, wherein the processor-executable instructions comprise a graphical user interface.

* * * * *